United States Patent [19]

Fitts et al.

[11] Patent Number: 4,696,898
[45] Date of Patent: Sep. 29, 1987

[54] VECTOR ENCODING HEPATITIS B SURFACE ANTIGEN

[75] Inventors: Renee A. Fitts, Framingham; Nancy Hsiung, Wellesley, both of Mass.; Dean H. Hamer, Washington, D.C.

[73] Assignee: Integrated Genetics, Inc., Framingham, Mass.

[21] Appl. No.: 570,940

[22] Filed: Jan. 16, 1984

[51] Int. Cl.⁴ .................. C12P 21/00; C12N 15/00; C12N 5/00; C12N 1/00
[52] U.S. Cl. ............................... 435/68; 435/240; 435/172.3; 435/320; 935/32; 935/70
[58] Field of Search ............ 435/317, 68, 172.3, 435/240, 241; 935/9, 10, 22, 41; 536/27–29

[56] References Cited

U.S. PATENT DOCUMENTS 4,419,446  12/1983  Howley et al. .............. 435/68
4,511,652   4/1985  Fogel et al. .................. 435/29

OTHER PUBLICATIONS

Pavlakis et al 1983, "Regulation of a Metallothionein--Growth Hormone Hybrid Gene in Bovine Papilloma Virus *Proc. Natl Acad Sci,* v80 397–401.
Mayo et al 1982, "The Mouse Metallothionein-1 Gene is Transcriptionally Regulated by Cadmium Following Transfection into Human or Mouse Cells" *Cell* v29 99–108.
Burrell et al 1979, "Expression in *E. Coli* of Hepatitis B virus DNA Sequences Cloned in Plasmid pBR322" *Nature,* v279 pp. 43–47.
Hamer et al 1982, "Induction of a Mouse Metallothionein-1 Gene in Animal Virus Vectors" in *Eukaryotic Viral Vectors* Cold Spring Harbor Lab., pp. 7–12.
Hamer et al 1982, "Regulation *In Vivo* of a Cloned Mammalian Gene: Cadmium Induces the Transcription of a Mouse Metallothionein Gene . . . " *J. Mol. App Gen* v1, 273–288.

*Primary Examiner*—Blondel Hazel

[57] ABSTRACT

Recombinant DNA vector including (1) a promoter for a eukaryotic metalliothionein gene ligated to a gene sequence encoding hepatitis B surface antigen, and (2) at least the 69% transforming region of the bovine papilloma genome, expression of the hepatitis B surface antigen encoding gene sequence being under the control of the metallothionein promoter.

11 Claims, 1 Drawing Figure

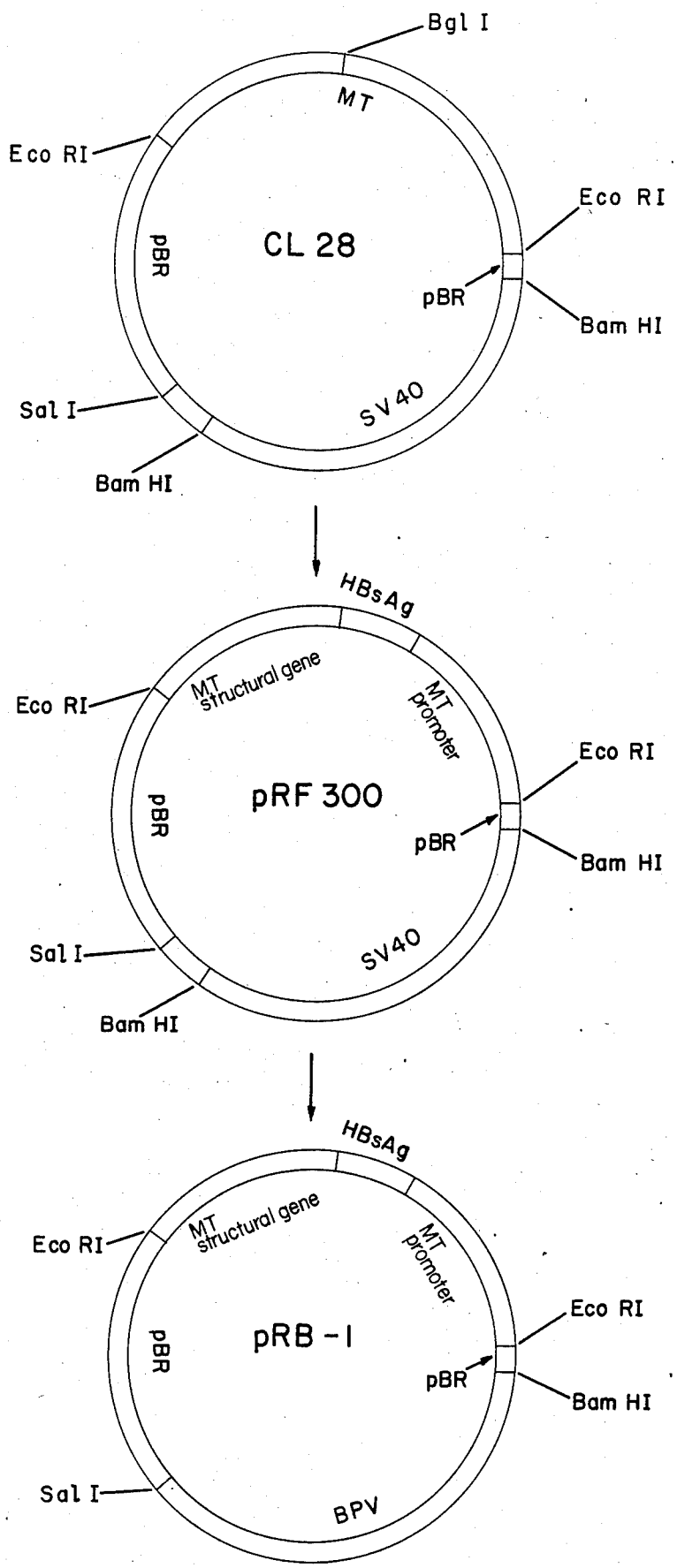

VECTOR ENCODING HEPATITIS B SURFACE ANTIGEN

BACKGROUND OF THE INVENTION

This invention relates to the use of recombinant DNA techniques to produce hepatitis B surface antigen (HBsAg).

Hepatitis B virus (HBV) is the infectious agent of serum hepatitis. Infection by this virus is a worldwide health problem; carriers of HBV can suffer from transient or chronic infection, the latter having the potential of progressing to liver cancer. The HBV infectious agent has been identified as the 42 nm Dane particle which contains a lipoprotein coat of hepatitis surface antigen surrounding an internal core particle consisting of a DNA polymerse and the 3200 base pair (bp) DNA genome. HBsAg is found in the serum of HBV carriers mainly in the form of 22 nm spherical particles or filaments and is observed to be the major target for the HBV neutralizing antibody. The 22 nm particles contain two polypeptides of apparent molecular weights of 22,000 and 27,000 daltons. These polypeptides are probably identical, differing only in the presence of glycosylation in the larger peptide. Because of the clinical importance of developing vaccines against HBsAg, a major effort has been undertaken by a number of laboratories to isolate HBsAg protein.

The HBV gene has been cloned into *Escherischia coli* and the complete nucleotide sequence has been determined, e.g., by Burrel et al. (1979) Nature 279, 43. The HBV DNA is a partially double stranded molecule with a single-stranded gap in one strand (L) and DNA of variable length in the second strand. The HBsAg gene has been cloned in *Escherischia coli* and has been shown to contain an open reading frame of 680 bp with no intervening sequences. A variety of systems have been employed in order to transfer the HBsAg DNA sequences into a host cell and obtain expression of HBsAg. Varying levels of HBsAg expression have been detected in yeast and mammalian cells transformed with viral vectors such as SV40 and retroviruses. For example, Moriarty et al. 1981 Proc. Natl. Acad. Sci. 78 2606–2610 and Liu et al. 1982 DNA (1) 213–221 describe SV40 vectors that contain the HBsAg gene and are capable of transforming cultured mammalian cells.

Pending U.S. patent application, Hamer et al., Ser. No. 452,783, filed Dec. 23, 1982, entitled "Human Growth Hormone Produced by Recombinant DNA in Mouse Cells", describes a mouse metallothionein (MT)—human growth hormone hybrid gene cloned in a bovine papilloma virus (BPV) vector. Expression of human growth hormone is induced by cadmium or another heavy metal, e.g., zinc. Hamer et al. says, p. 5, that "[t]his vector should be useful for introducing other nonselectable genes into cultured cells, e.g., genes for . . . virus gene products that could be used as vaccines (such as hepatitis B surface antigen)".

Sarver et al (1981) Mol. and Cell. Biol. 1, 486–496; DiMaio (1982) P.N.A.S. USA 79, 4030–4034; and Zinn et al. (1982) P.N.A.S. USA 79, 4897–4901 describe BPV vectors which express, respectively, rat preproinsulin, human beta-globin, and human beta-interferon when used to transform mammalian cells.

SUMMARY OF THE INVENTION

In general, the invention features a recombinant DNA vector including (1) a promoter for a eukaryotic metallothionein gene ligated to a gene sequence encoding hepatitis B surface antigen, and (2) at least the 69% transforming region of the bovine papilloma virus genome, expression of the hepatitis B surface antigen encoding gene sequence being under the control of the metallothionein promoter.

In preferred embodiments, mouse C127 cells transformed by the vector are capable of continuously (without passage) producing hepatitis B surface antigen for at least 60 days, most preferably at least 80 days; the vector is capable of being maintained in transformed mouse C127 cells extrachromasomally in multiple copies; mouse C127 cells transformed with the vector are capable of producing hepatitis B surface antigen at a level of at least 5 mg/L (liter of culture medium)/24 hr, most preferably at least 10 mg/L/24 hr, without induction by a heavy metal; production of hepatitis B surface antigen without induction by a heavy metal is at least as great as production of hepatitis B surface antigen by the same system in the presence of cadmium; the vector includes all of the metallothionein gene; the metallothionein gene is a mouse metallothionein gene; and the host cell is a rodent fibroblast cell, most preferably a mouse C127 cell or an NIH 3T3 cell.

Mammalian cells transformed by the vector of the invention are capable of being cultured continuously for a long period of time without passage or cell death; the present system thus allows the continuous harvesting of HBsAg without the need for restarting the culture every time harvesting is carried out. The continuous process thus makes collection of the antigen convenient and reduces the frequency with which fresh cultures must be initiated. Furthermore, the plasmid of the invention is maintained at high copy number in cultured cells, amplifying the HBsAg gene. HBsAg is expressed under control of the MT promoter.

Levels of HBsAg production by transformed cell lines of the invention are high, ranging from 5 mg/L/24 hr to over 10 mg/L/24 hr.

High levels of HBsAg expression are obtained in transformed cells without induction by cadmium or any other heavy metal, e.g., zinc. Cell cultures can thus be prepared without the necessity of handling toxic substances, and purification of hepatitis B surface antigen is not complicated by the presence of toxic metals in the growth medium.

Other features and advantages of the invention will be apparent from the following description of the preferred embodiment thereof, and from the claims.

DESCRIPTION OF THE PREFERRED EMBODIMENT

We now turn to a description of the preferred embodiment of the invention, after first briefly describing the drawing.

Drawing

The FIGURE is a diagrammatic representation of the construction of plasmids pRF300 and pRB-1.

Structure

The plasmid illustrated as plasmid pRB-1 in the FIGURE contains a hybrid gene produced by the insertion of the HBsAg-encoding gene into the mouse MT gene between the MT promoter and the MT structural gene. Plasmid pRB-1 also contains the entire BPV genome, which causes the vector to transform mammalian cells.

Synthesis

The vector of the invention is constructed using recombinant DNA techniques known in the art. A plasmid containing an MT gene and a lytic viral genome is digested with an endonuclease restriction enzyme. A gene encoding human HBsAg is then inserted within the MT gene between the MT promoter and the MT structural gene. This intermediate plasmid, containing the MT-HBsAg hybrid gene and the lytic viral genome, is digested to excise the lytic viral genome, which is then replaced by the BPV genome. The resulting plasmid contains the MT-HBsAg hybrid gene and the BPV genome.

Construction of pRB-1

All plasmids are transformed into and maintained in E. coli strain MC 1061. Referring to the FIGURE, plasmid CL28 (referred to as PJYMMTC(E) in Hamer et al. (1983) J. Mol. Applied Gen. 1, 273), containing the mouse MT gene and the SV40 genome, is digested with Bgl II endonuclease restriction enzyme, opening the plasmid between the promoter region and the structural sequence of the MT gene. The 1.35 kb human HBsAg gene-containing Bam HI fragment from plasmid SuAM115 (a pBR-SV40-HBsAg plasmid described in Moriarty et al. (1981) P.N.A.S. USA 78, 2605) is then cut out and inserted at the Bgl II site of CL28 to form pRF300. The SV40 and some pBR sequences in pRF300 are then removed by Bam HI digestion; further digestion with Sal I enzyme yields a linear molecule with Bam HI and Sal I ends.

Plasmid B2-2 (not shown), containing the entire BPV genome, is digested with Bam HI and Sal I enzymes (Any source of the BPV genome can be used; BPV is available, for example, from New England Biolabs; B2-2 was used here only because it has a convenient Sal I site). The excised BPV-containing fragment, which also contains pBR DNA, is ligated to the HBsAg-MT hybrid gene-containing linear Bam HI-Sal I fragment. The resulting plasmid, pRB-1, consists of the entire BPV genome and the HBsAg structural gene inserted within the MT gene between the promoter and the remainder of the MT gene.

Transformation of Mammalian Cells pRB-1 plasmid DNA is introduced into mouse C127 cells using a modification of the transfection technique of Wigler et al. (1977) Cell 11, 223, as follows.

5 ug of pRB-1 DNA is added to 0.5 ml of a 240 mM $CaCl_2$ solution containing 10 ug of carrier salmon sperm DNA. This solution is bubbled into an equal volume of 2×HBS (280 mM NaCl, 50 mM Hepes, and 1.5 mM sodium phosphate) having a pH of 7.1. The calcium phosphate is allowed to form for 30 minutes at room temperature, and $5 \times 10^5$ C127 cells are plated 24 hrs. prior to transfection. While the calcium phosphate precipitate is forming, the cell growth medium is changed. The calcium phosphate precipitate is added to the cells and incubated for 6-8 hr. at 37° C. The DNA is removed and the cells are exposed to 20% glycerol in phosphate buffered saline (PBS), pH 7, for 1-2 minutes at room temperature. The cells are washed with PBS, and 10 ml of Dulbecco's modified medium with 10% fetal calf serum (MA Biologicals), penicillin/streptomycin and 10 mM glutamine (GIBCO) is added. The medium is changed 24 hrs. later and every 3-4 days thereafter. Foci can be detected after 10-14 days and isolated by the cloning ring method after 21 days. The foci are expanded for analysis. Mouse C127 cells transformed with pRB-1 were deposited in the American Type Culture Collection, Rockville, MD, and given ATCC Accession No. CRL 8399.

Use

Transformed cells are cultured using conventional techniques, and HBsAg is harvested continuously from the culture medium, using conventional techniques, and is used to prepare hepatitis B vaccine, or for biochemical assays, also using well-known techniques.

HBsAg is secreted into the culture medium as 22 nm particles which can be observed in electromicrographs of the media.

pRB-1-transformed mouse C127 cells can exist for up to 85 days in confluent cell culture if the media is changed every 24-48 hr. The cells continually double, in the flask or roller bottle, with growth characteristics of transformed cells. We conclude that the combination of a strong metallothionein promoter controlling HBsAg production in the BPV vector (which allows amplified DNA copy number) and the continuous growth properties of the BPV transformed cells provide an optimal system for scale up production of the HBsAg.

OTHER EMBODIMENTS

Other embodiments are within the following claims. For example, although the use of all of the BPV genome is preferred, just the 69% transforming region can also be used. However, when only the 69% region is used, there can be undesirable interactions between the plasmid and the chromosome of the host cell, i.e., much of the plasmid DNA can incorporate into the chromosone rather than remaining episomal, so that the plasmid is very difficult to retrieve from the cells. Also, if less than the entire BPV genome is used, the pBR region which is frequently attached to BPV (since BPV is normally provided as part of a pBR322-derived plasmid), must be cut out prior to transfection, because the pBR region, in a less than complete BPV fragment, can have an inhibitory effect on transfection, while this does not occur when using all of BPV. Undersirable rearrangements can also occur when using only the 69% region.

It is preferable that the eukaryotic metallothionein promoter be of mammalian, most preferably murine, origin, but any suitable metallothionein promoter can be used (each mammalian species which produces a metallothionein apparently does so using a structurally different gene).

To construct a vector within the invention, other than pRB-1, cell line DNA can be used as the source of the MT promoter and structural gene, the HBsAg gene, and the BPV genome, and those genetic elements can be inserted, using conventional recombinant DNA techniques, into a desired vector.

Any suitable host cells can be used. For example, other rodent fibroblast cell lines which can be infected by BPV can be used; for example, NIH 3T3 cells (ATCC CCL 92) can be used.

We claim:

1. A recombinant DNA vector comprising (1) a promoter for a eukaryotic metallothionein gene ligated to a gene sequence encoding human hepatitis B surface antigen, and (2) at least the 69% transforming region of the bovine papilloma virus genome, expression of said hepatitis B surface antigen encoding gene sequence being under the control of said metallothionein promoter.

2. The vector of claim 1 wherein said vector comprises all of said bovine papilloma virus genome.

3. The vector of claim 1, said vector comprising all of said metallothionein gene, wherein said gene sequence encoding hepatitis B surface antigen is inserted in said metallotionein gene between said promoter and the remainder of said metallothionein gene.

4. The vector of claim 1 wherein said metallothionein gene is a mouse metallothionein gene.

5. A mammalian cell transformed with a recombinant DNA vector comprising (1) a promoter for a eukaryotic metallothionein gene ligated to a gene sequence encoding human hepatitis B surface antigen, and (2) at least the 69% transforming region of the bovine papilloma virus genome, expression of said hepatitis B surface antigen encoding gene sequence being under the control of said metallothionein promoter.

6. The mammalian cell of claim 5, wherein said cell is a rodent fibroblast cell.

7. The cell of claim 6, wherein said cell is mouse C127 cell.

8. The cell of claim 6, wherein said cell is an NIH 3T3 cell.

9. A process for producing human hepatitis B surface antigen comprising culturing the cell of claim 5 in culture medium and harvesting said human hepatitis B surface antigen from said culture medium.

10. A cell exhibiting the characteristics of the cells assigned ATCC Accession No. CRL 8399.

11. A plasmid exhibiting the characteristics of the transforming plasmid incorporated into the cells assigned ATCC Accession No. CRL 8399.

* * * * *

UNITED STATES PATENT AND TRADEMARK OFFICE
CERTIFICATE OF CORRECTION

PATENT NO. : 4,696,898  Page 1 of 2
DATED : September 29, 1987
INVENTOR(S) : Renee A. Fitts et al.

It is certified that error appears in the above-identified patent and that said Letters Patent are hereby corrected as shown below:

On the Title Page:

On the cover sheet in section [56], please add to the list of "Other Publications":

"Moriaty et al. (1981) Proc. Natl. Acad. Sci. USA 78(4), 2606-2610;

Liu et al. (1982) Mary Ann Liebert 1(1) 213-221;

Hamer et al. Patent Application "Human Growth Hormone Produced by Recombinant DNA in Mouse Cells";

Sarver et al. (1981) Molecular and Cellular Biology, 1(6), 486-496;

DiMaio et al. (1982) Proc. Natl. Acad. Sci. USA, 79, 4030-4034

Zinn et al. (1982) Proc. Natl. Acad. Sci. 79 4897-4901

Hamer et al. Patent Application "A Simian Virus Recombinant That Directs the Synthesis or Hepatitis B Surface Antigen"

Col. 1, line 17, replace "polymerse" with --polymerase--.

Col. 4, line 31, replace "chromosone" with --chromosome--.

UNITED STATES PATENT AND TRADEMARK OFFICE
CERTIFICATE OF CORRECTION

PATENT NO. : 4,696,898

DATED : September 29, 1987

INVENTOR(S) : Renee A. Fitts et al.

It is certified that error appears in the above-identified patent and that said Letters Patent is hereby corrected as shown below:

Col. 5, line 4, replace "metalloitionein" with

--metallothionein--.

Signed and Sealed this

Ninth Day of August, 1988

Attest:

DONALD J. QUIGG

Attesting Officer

Commissioner of Patents and Trademarks